United States Patent
Hirakawa et al.

(10) Patent No.: US 11,688,498 B2
(45) Date of Patent: Jun. 27, 2023

(54) MEDICAL DOCUMENT DISPLAY CONTROL APPARATUS, MEDICAL DOCUMENT DISPLAY CONTROL METHOD, AND MEDICAL DOCUMENT DISPLAY CONTROL PROGRAM

(71) Applicant: FUJIFILM Corporation, Tokyo (JP)

(72) Inventors: Shinnosuke Hirakawa, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 80 days.

(21) Appl. No.: 17/037,581

(22) Filed: Sep. 29, 2020

(65) Prior Publication Data
US 2021/0012870 A1    Jan. 14, 2021

Related U.S. Application Data

(63) Continuation of application No. PCT/JP2019/011879, filed on Mar. 20, 2019.

(30) Foreign Application Priority Data

Apr. 4, 2018    (JP) .................................. 2018-072524

(51) Int. Cl.
*G16H 15/00*    (2018.01)
*G16H 30/40*    (2018.01)
(Continued)

(52) U.S. Cl.
CPC .............. *G16H 15/00* (2018.01); *A61B 6/032* (2013.01); *A61B 6/461* (2013.01); *G06F 40/166* (2020.01); *G16H 30/40* (2018.01)

(58) Field of Classification Search
CPC ........ G16H 15/00; G16H 30/40; G16H 50/20; A61B 6/032; A61B 6/461; A61B 6/563;
(Continued)

(56) References Cited

U.S. PATENT DOCUMENTS 8,542,249 B2    9/2013    Ishida et al.
2002/0021828 A1    2/2002    Papier et al.
(Continued)

FOREIGN PATENT DOCUMENTS

EP    2710958    3/2014
JP    2004517380    6/2004
(Continued)

OTHER PUBLICATIONS

"Search Report of Europe Counterpart Application", dated Apr. 19, 2021, pp. 1-9.
(Continued)

*Primary Examiner* — Stephen S Hong
*Assistant Examiner* — Ahamed I Nazar
(74) *Attorney, Agent, or Firm* — JCIPRNET (57) ABSTRACT

The medical document display control apparatus includes a reception unit that receives observation information on a subject, an acquisition unit that acquires relation information on an analysis result obtained by immediately analyzing the observation information received by the reception unit, and a display control unit that immediately displays the relation information acquired by the acquisition unit on a display unit.

8 Claims, 7 Drawing Sheets

(51) Int. Cl.
*G06F 16/93* (2019.01)
*A61B 5/00* (2006.01)
*G06F 40/166* (2020.01)
*A61B 6/03* (2006.01)
*A61B 6/00* (2006.01)

(58) Field of Classification Search
CPC ........... A61B 5/00; A61B 5/055; A61B 6/566; G06F 40/166
USPC .......... 715/968; 382/195, 199, 159; 707/769
See application file for complete search history.

(56) References Cited

U.S. PATENT DOCUMENTS

| | | | | |
|---|---|---|---|---|
| 2006/0173717 A1* | 8/2006 | Scheuner | ............... | G16H 50/70 600/300 |
| 2007/0299696 A1* | 12/2007 | Matsubara | ............. | G16H 10/60 705/3 |
| 2009/0076853 A1* | 3/2009 | Sagawa | .................. | G16H 15/00 705/3 |
| 2009/0221881 A1* | 9/2009 | Qian | ....................... | G16H 30/20 382/199 |
| 2009/0248441 A1* | 10/2009 | Okada | .................... | G06Q 10/10 715/764 |
| 2010/0053213 A1* | 3/2010 | Ishida | .................... | G16H 15/00 345/660 |
| 2010/0138239 A1 | 6/2010 | Reicher et al. | | |
| 2014/0013219 A1* | 1/2014 | Liu | ........................ | G06F 40/56 715/255 |
| 2014/0343925 A1 | 11/2014 | Mankovich et al. | | |
| 2015/0278452 A1* | 10/2015 | Neff | ........................ | G16Z 99/00 705/3 |
| 2015/0294083 A1* | 10/2015 | Yokokubo | ............... | G16H 70/40 705/2 |
| 2016/0012319 A1* | 1/2016 | Mabotuwana | ......... | G16H 30/40 382/128 |
| 2016/0048651 A1* | 2/2016 | Papier | .................... | G16H 30/20 382/128 |
| 2017/0329904 A1* | 11/2017 | Naughton | .............. | G16B 50/10 |

FOREIGN PATENT DOCUMENTS

| | | |
|---|---|---|
| JP | 2008250543 | 10/2008 |
| JP | 2009078085 | 4/2009 |
| JP | 2010057528 | 3/2010 |
| JP | 2014016990 | 1/2014 |
| JP | 2015506511 | 3/2015 |

OTHER PUBLICATIONS

"International Search Report (Form PCT/ISA/210) of PCT/JP2019/011879," dated Jun. 18, 2019, with English translation thereof, pp. 1-5.

"Written Opinion of the International Searching Authority (Form PCT/ISA/237) of PCT/JP2019/011879," dated Jun. 18, 2019, with English translation thereof, pp. 1-9.

"Office Action of Japan Counterpart Application" with English translation thereof, dated Dec. 7, 2021, p. 1-p. 6.

"Decision of Refusal of Japan Counterpart Application", dated May 31, 2022, with English translation thereof, p. 1-p. 2.

\* cited by examiner

| OBSERVATION INFORMATION | REFERENCE INFORMATION |
|---|---|
| CANCER | ELECTRONIC MEDICAL RECORD |
| LEFT LUNG | ANATOMICAL CLASSIFICATION |
| SIZE | PAST REPORT |
| ⋮ | ⋮ |

| MARCH 5, 2018 |
| FINDINGS |
| LEFT LUNG —41 |

FIG. 10

RELATION INFORMATION

44— UPPER LOBE    $S^{1+2}$: APICOPOSTERIOR SEGMENT $S^3$: ANTERIOR SEGMENT $S^4$: SUPERIOR LINGULAR SEGMENT $S^5$: INFERIOR LINGULAR SEGMENT 45— LOWER LOBE    $S^6$: UPPER-LOWER LOBE SEGMENT ⋮      ⋮

$S^8$: ANTERIOR BASAL LOBE SEGMENT $S^9$: LATERAL BASAL LOBE SEGMENT

MEDICAL DOCUMENT DISPLAY CONTROL APPARATUS, MEDICAL DOCUMENT DISPLAY CONTROL METHOD, AND MEDICAL DOCUMENT DISPLAY CONTROL PROGRAM

CROSS-REFERENCE TO RELATED APPLICATION

The present application is a continuation application of International Application No. PCT/JP2019/011879, filed Mar. 20, 2019, which claims priority to Japanese Patent Application No. 2018-072524, filed Apr. 4, 2018. The contents of these applications are incorporated herein by reference in their entirety.

BACKGROUND

Field of the Invention

The present invention relates to a medical document display control apparatus, a medical document display control method, and a medical document display control program.

Related Art

In recent years, advances in medical apparatuses, such as computed tomography (CT) apparatuses and magnetic resonance imaging (MRI) apparatuses, have enabled image diagnosis using high-resolution three-dimensional medical images with higher quality. In particular, since a region of a lesion can be accurately specified by image diagnosis using CT images, MRI images, and the like, appropriate treatment can be performed based on the specified result.

A medical image is analyzed by computer-aided diagnosis (CAD) using a discriminator learned by deep learning or the like, regions, positions, volumes, and the like of lesions included in the medical image are extracted, and these are acquired as the analysis result. The analysis result generated by analysis processing in this manner is stored in a database so as to be associated with examination information, such as a patient name, gender, age, and a modality that has acquired the medical image, and provided for diagnosis. At this time, a radiology technician who acquired medical images determines a radiologist according to the medical image and informs the determined radiologist that the medical image and the CAD analysis result are present. The radiologist interprets the medical image with reference to the transmitted medical image and analysis result and creates an interpretation report in his or her own interpretation terminal apparatus.

In a case where a diagnostician, a radiologist, or the like creates a medical document such as an interpretation report, the diagnostician, the radiologist, or the like may refer to patient information identifying an individual, order information such as a type or item of an examination, and accessory information such as a result of an examination performed in the past, which are displayed on a screen in addition to the medical image. However, in the accessory information, there are essential items and non-essential items, and in a case where all the items are displayed on the screen, it is difficult for the diagnostician, the radiologist, or the like who are observers of the display screen, to understand where the essential items are displayed and to grasp contents of the essential items. Therefore, JP2010-057528A and JP2009-078085A disclose a medical image display apparatus in which items having higher importance are displayed on the screen in order of priority.

On the other hand, in a case where an operator such as a diagnostician and a radiologist creates a medical document such as an interpretation report, accessory information to be referred to may differ depending on the analysis result of the medical image input as a finding. For example, in a case where a lesion having a deep genetic correlation is detected in the medical image, an operator wants to refer to a family medical history. In addition, in a case where a lesion is detected at a part, the operator wants to instantly refer to the name of an anatomically classified region at a part in order to input a more accurate location in the part of the lesion. However, in the method described in JP2010-057528A and JP2009-078085A, since only the items having higher importance are displayed on the screen in order of priority on the basis of predetermined importance, the accessory information currently desired by the operator may not be displayed on the screen.

SUMMARY

The present invention has been made in view of the above circumstances, and an object of the present invention is to be able to display information currently desired by an operator such as a diagnostician or a radiologist in real time.

A medical document display control apparatus according to the embodiment of the present invention includes a reception unit that receives observation information on a subject, an acquisition unit that acquires relation information on an analysis result obtained by immediately analyzing the observation information received by the reception unit, and a display control unit that immediately displays the relation information acquired by the acquisition unit on a display unit.

In the medical document display control apparatus according to the embodiment of the present invention, the display control unit may summarize the relation information and display the relation information on the display unit.

In the medical document display control apparatus according to the embodiment of the present invention, the display control unit may display the relation information for each item on the display unit.

In the medical document display control apparatus according to the embodiment of the present invention, the item may be an anatomically classified region.

In the medical document display control apparatus according to the embodiment of the present invention, the item may be a blood relative.

In the medical document display control apparatus according to the embodiment of the present invention, the relation information may be information on another subject different from the subject.

In the medical document display control apparatus according to the embodiment of the present invention, the reception unit may receive observation information based on an analysis result of a medical image of the subject.

In the medical document display control apparatus according to the embodiment of the present invention, the observation information may be information representing findings.

In the medical document display control apparatus according to the embodiment of the present invention, the information representing the findings may be information including at least one of a type of a lesion, a position of a lesion, or a size of a lesion.

A medical document display control method according to the embodiment of the present invention includes receiving observation information on a subject, acquiring relation information on an analysis result obtained by immediately analyzing the received observation information, and immediately displaying the relation information on a display unit.

A medical document display control program according to the embodiment of the present invention causes a computer to execute a procedure for receiving observation information on a subject, a procedure for acquiring relation information on an analysis result obtained by immediately analyzing the received observation information, and a procedure for immediately displaying the acquired relation information on a display unit.

The medical document display control apparatus according to the embodiment of the present invention comprises a memory that stores instructions for a computer to execute, and a processor that is configured to execute stored instructions, in which the processor receives the observation information on the subject, acquires the relation information on the analysis result obtained by immediately analyzing the received observation information, and executes processing of immediately displaying the relation information on the display unit.

The present invention includes receiving the observation information on the subject, acquiring the relation information on the analysis result obtained by immediately analyzing the received observation information, and immediately displaying the relation information on the display unit. Therefore, the relation information derived from the observation information input by the operator such as the diagnostician and the radiologist can be displayed on the display unit in real time as the information currently desired by the operator such as the diagnostician and the radiologist. Accordingly, the operator can visually recognize the desired information in real time.

DETAILED DESCRIPTION

Hereinafter, an embodiment of the invention will be described with reference to the accompanying diagrams.

Figure 1:
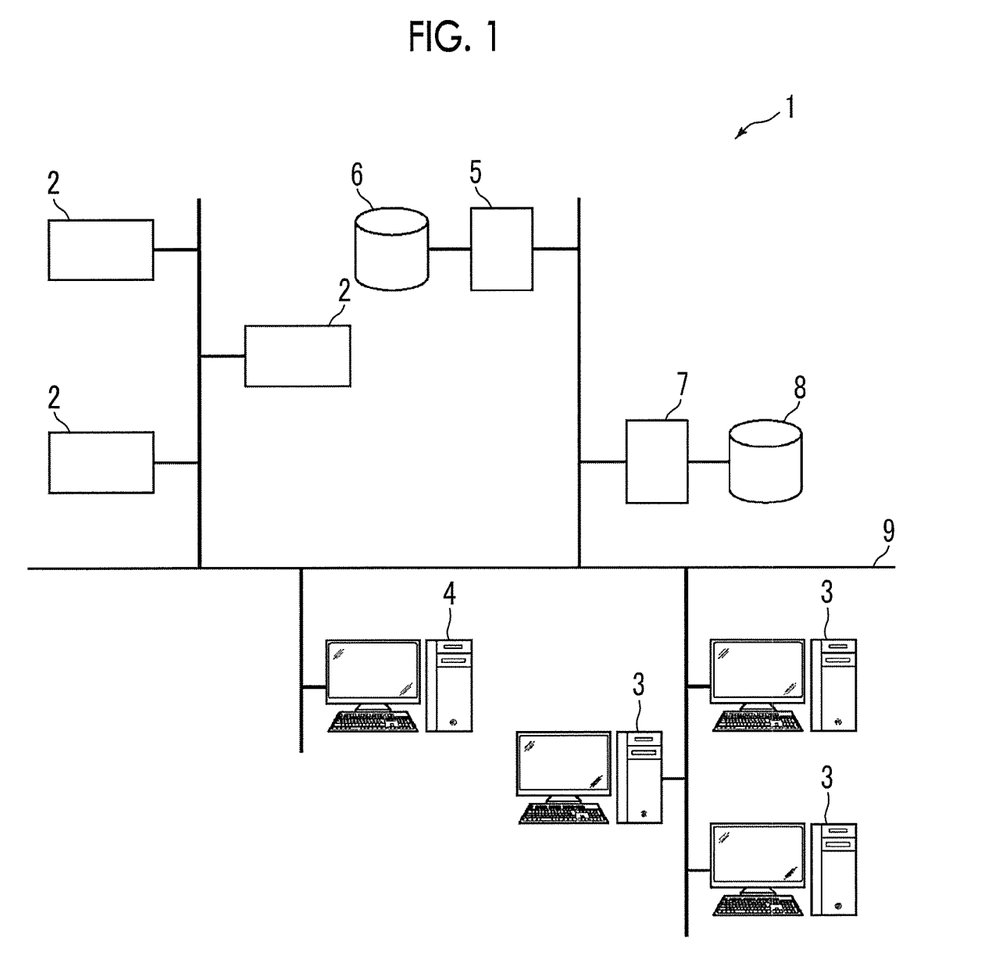
FIG. 1 is a diagram showing a schematic configuration of a medical information system to which a medical document display control apparatus according to an embodiment of the invention is applied.

FIG. 1 is a diagram showing a schematic configuration of a medical information system to which a medical document display control apparatus according to an embodiment of the invention is applied. A medical information system 1 shown in FIG. 1 is a system for performing imaging of an examination target part of an examinee, storage of a medical image acquired by imaging, interpretation of a medical image by a radiologist and creation of an interpretation report, and viewing of an interpretation report by a diagnostician in a medical department of a request source and detailed observation of a medical image to be interpreted, on the basis of an examination order from a diagnostician (doctor) in a medical department using a known ordering system. As shown in FIG. 1, the medical information system 1 is configured to include a plurality of modalities (imaging apparatuses) 2, a plurality of interpretation workstations (WS) 3 that are interpretation terminals, a medical department workstation (WS) 4, an image server 5, an image database 6, an interpretation report server 7, and an interpretation report database 8 that are communicably connected to each other through a wired or wireless network 9.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed onto the computer from the recording medium. Alternatively, the application program is stored in a storage apparatus of a server computer connected to the network 9 or in a network storage so as to be accessible from the outside, and is downloaded and installed onto the computer as necessary.

A modality 2 is an apparatus that generates a medical image showing a diagnosis target part by imaging the diagnosis target part of the examinee. Specifically, the modality 2 is a simple X-rays imaging apparatus, a CT apparatus, an MRI apparatus, a positron emission tomography (PET) apparatus, and the like. A medical image generated by the modality 2 is transmitted to the image server 5 and stored therein.

An interpretation WS 3 includes the medical document display control apparatus according to the present embodiment. The configuration of the interpretation WS 3 will be described later.

A medical department WS 4 is a computer used by a diagnostician in a medical department to observe the details of an image, view an interpretation report, create an electronic medical record, and the like, and is configured to include a processing apparatus, a display apparatus such as a display, and an input apparatus such as a keyboard and a mouse. In the medical department WS 4, each processing, such as the creation of a medical record of patient (electronic medical record), sending a request to view an image to the image server 5, display of an image received from the image server 5, automatic detection or highlighting of a lesion-like portion in an image, sending a request to view an interpretation report to the interpretation report server 7, and display of an interpretation report received from the interpretation report server 7, is performed by executing a software program for each processing.

The image server 5 is obtained by installing a software program for providing a function of a database management system (DBMS) on a general-purpose computer. The image server 5 comprises a storage for an image database 6. This storage may be a hard disk apparatus connected to the image server 5 by a data bus, or may be a disk apparatus connected to a storage area network (SAN) or a network attached storage (NAS) connected to the network 9. In a case where the image server 5 receives a request to register a medical image from the modality 2, the image server 5 registers the medical image in the image database 6 in a format for a database.

Image data of the medical images acquired by the modality 2 or a medical image group including a plurality of medical images and accessory information are registered in the image database 6. The accessory information includes, for example, an image ID for identifying each medical image or a medical image group (hereinafter, may be simply referred to as a medical image), a patient identification (ID) for identifying an examinee, an examination ID for identifying an examination, a unique ID (UID: unique identification) allocated for each medical image, examination date and examination time at which the medical image or the medical image group is generated, the type of a modality used in an examination for acquiring a medical image, patient information such as the name, age, and gender of patient, an examination part (imaging part), imaging information (an imaging protocol, an imaging sequence, an imaging method, imaging conditions, the use of a contrast medium, and the like), and information such as a series number or a collection number in a case where a plurality of medical images are acquired in one examination.

In a case where a viewing request from the interpretation WS 3 is received through the network 9, the image server 5 searches for a medical image registered in the image database 6 and transmits the searched medical image to the interpretation WS 3 that is a request source.

The interpretation report server 7 has a software program for providing a function of a database management system to a general-purpose computer. In a case where the interpretation report server 7 receives a request to register an interpretation report from the interpretation WS 3, the interpretation report server 7 registers the interpretation report in the interpretation report database 8 in a format for a database. In a case where a request to search for an interpretation report is received, the interpretation report is searched for from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, and findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the internet or a dedicated circuit. In any case, it is preferable that the network 9 is configured to be able to realize high-speed transmission of medical images, such as an optical network.

Hereinafter, the interpretation WS 3 according to the present embodiment will be described in detail. The interpretation WS 3 is a computer used by a radiologist of a medical image to interpret the medical image and create the interpretation report, and is configured to include a processing apparatus, a display apparatus such as a display, and an input apparatus such as a keyboard and a mouse. In the interpretation WS 3, each process, such as making a request to view a medical image to the image server 5, various kinds of image processing on a medical image received from the image server 5, display of a medical image, analysis processing on a medical image, highlighting of a medical image based on the analysis result, creation of an interpretation report based on the analysis result, support for the creation of an interpretation report, making a request to register an interpretation report and a request to view an interpretation report to the interpretation report server 7, and display of an interpretation report received from the interpretation report server 7, is performed by executing a software program for each processing. It should be noted that since processing other than processing performed by the medical document display control apparatus of the present embodiment, among these processes, are performed by a known software program, the detailed description thereof will be omitted herein. In addition, the processing other than the processing performed by the medical document display control apparatus of the present embodiment may not be performed in the interpretation WS 3, and a computer that performs the processes may be separately connected to the network 9, and requested processing on the computer may be performed according to a processing request from the interpretation WS 3.

The interpretation WS 3 includes the medical document display control apparatus according to the present embodiment. Therefore, a medical document display control program according to the present embodiment is installed on the interpretation WS 3. The medical document display control program is recorded on a recording medium, such as a DVD or a CD-ROM, and distributed, and is installed onto the interpretation WS 3 from the recording medium. Alternatively, the medical document display control program is stored in a storage apparatus of a server computer connected to the network or in a network storage so as to be accessible from the outside, and is downloaded and installed onto the interpretation WS 3 as necessary.

Figure 2:
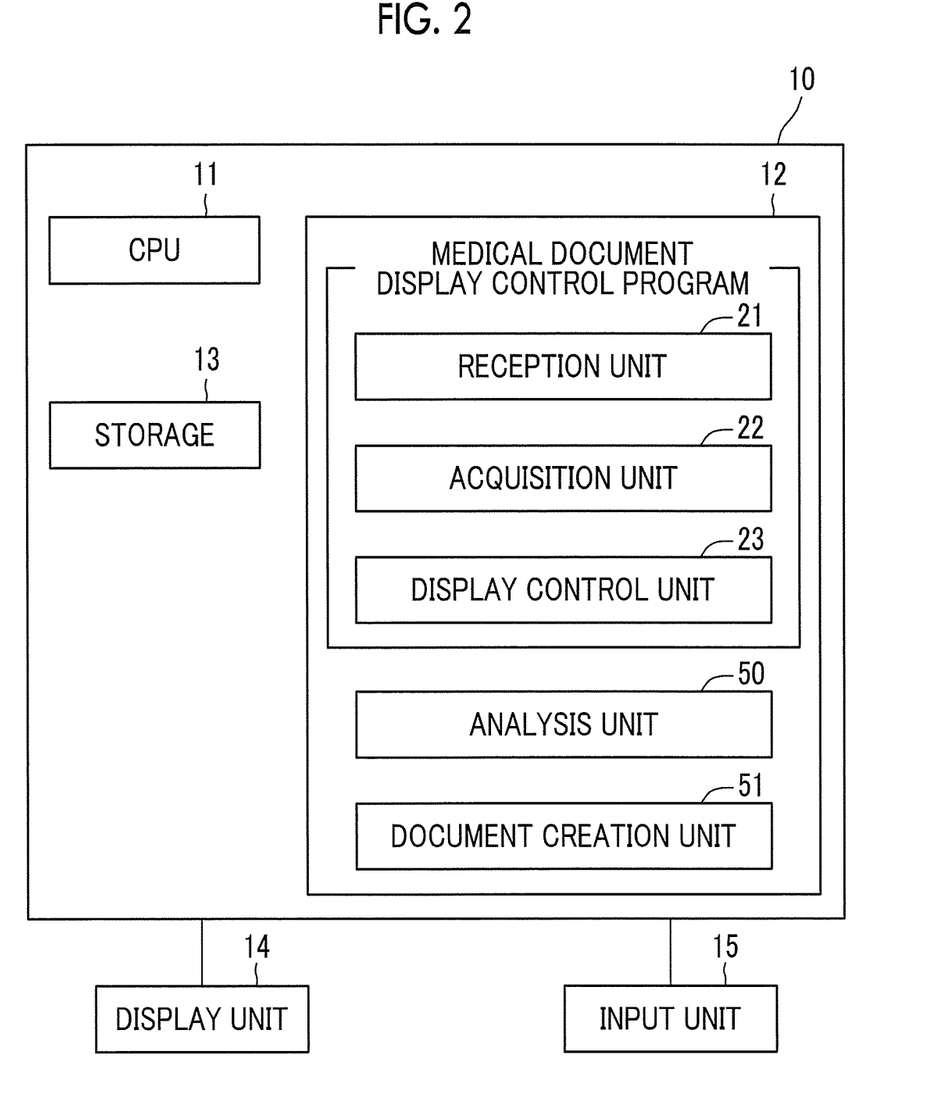
FIG. 2 is a diagram showing a schematic configuration of a medical document display control apparatus according to an embodiment of the present invention.

FIG. 2 is a diagram showing a schematic configuration of a medical document display control apparatus 10 according to the embodiment of the present invention that is realized by installing the medical document display control program. As shown in FIG. 2, the medical document display control apparatus 10 comprises a central processing unit (CPU) 11, a memory 12, and a storage 13 as the configuration of a standard computer. In addition, a display apparatus (hereinafter, referred to as a display unit) 14, such as a liquid crystal display, and an input apparatus (hereinafter, referred to as an input unit) 15, such as a keyboard and a mouse, are connected to the medical document display control apparatus 10. It should be noted that an input unit 15 may be one that receives an input by voice such as a microphone.

The storage 13 consists of a storage device, such as a hard disk or a solid state drive (SSD). Medical images and various kinds of information including information necessary for processing of the medical document display control apparatus 10, which are acquired from the image server 5 through the network 9, are stored in the storage 13.

The medical document display control program is stored in the memory 12. The medical document display control program defines, as processing to be executed by the CPU 11, reception processing that receives observation information on a subject, acquisition processing that acquires relation information on an analysis result obtained by immediately analyzing the received observation information, and display control processing that immediately displays the acquired relation information on the display unit.

In a case where the CPU 11 executes the processing in accordance with the medical document display control program, the computer functions as a reception unit 21, acquisition unit 22, and a display control unit 23. It should be noted that in the present embodiment, the CPU 11 executes the functions of each unit according to the medical document display control program. However, as a general-purpose processor that executes software to function as various processing units, a programmable logic device (PLD) that is a processor whose circuit configuration can be changed after manufacturing, such as a field programmable gate array (FPGA), can be used in addition to the CPU 11. Alternatively, the processing of each unit may also be executed by a dedicated electric circuit that is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units using one processor, first, as represented by a computer, such as a client and a server, there is a form which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. In this way, various processing units are formed using one or more of the above-mentioned various processors as hardware structures.

More specifically, the hardware structure of these various processors is an electrical circuit (circuitry) in the form of a combination of circuit elements, such as semiconductor elements.

It should be noted that in a case where the interpretation WS 3 functions as an apparatus other than the medical document display control apparatus 10 for performing processing, the memory 12 stores a program that executes the function. For example, in the present embodiment, an analysis program is stored in the memory 12 since the interpretation WS 3 performs the analysis processing. Therefore, in the present embodiment, the computer configuring the interpretation WS 3 also functions as an analysis unit 50 that executes the analysis processing.

The analysis unit 50 comprises a discriminator that is machine-learned to discriminate whether or not each pixel (voxel) in the medical image represents a lesion, and the type of the lesion. In the present embodiment, the discriminator consists of a neural network deep-learned such that a plurality of types of lesions included in the medical image can be classified. In a case where the medical image is input, the discriminator in the analysis unit 50 is learned so as to output the probability of each of a plurality of lesions to each pixel (voxel) in the medical image. Then, the discriminator obtains a lesion exceeding a predetermined threshold value and having the maximum probability for a certain pixel, and discriminates that the pixel is the pixel of the determined lesion.

It should be noted that the discriminator may be, for example, a support vector machine (SVM), a convolutional neural network (CNN), or a recurrent neural network (RNN) in addition to the neural network deep-learned.

In addition, the analysis unit 50 uses a discrimination result by the discriminator to specify a type of lesion, a position of the lesion, and a size of the lesion to generate an analysis result. For example, in a case where the medical image includes a thoracoabdominal part of the human body and a lesion is found in the thoracoabdominal part, the analysis unit 50 generates an analysis result including a type, a position, and a size of the lesion in the thoracoabdominal part. More specifically, the analysis unit 50 generates, as an analysis result, that there is a nodule of 23×19 mm in the lower lobe position S6*b* of the right lung, and that there is a nodule of 20×10 mm in the lower lobe position S6 of the left lung. In addition, in a case where a lesion is found, the analysis unit 50 includes information representing the storage location of the analyzed medical image in the image database 6 in the analysis result.

The analysis unit 50 also has a function of analyzing observation information received by the reception unit 21 to be described later. It should be noted that an analysis method of the observation information by the analysis unit 50 will be described in detail later.

In a case of creating a medical document for a medical image, a document creation unit 51 creates a medical document by inputting character information representing finding content for the medical image. Here, the document creation unit 51 has a document creating function such as converting an input character into Chinese character, and creates a document on the basis of an input from the input unit 15 by an operator. It should be noted that the document creation unit 51 creates a document by converting voice into characters in a case where input is made by the voice. Here, in the present embodiment, the interpretation report is created as the medical document. However, in the present invention, the medical document is not limited to an interpretation report, but includes documents such as a diagnosis report and an electronic medical record, and includes medical documents including (For example, an image) other than character information.

Here, in the present embodiment, the "medical image" is an image to be referred to at the time of creating the medical document such as the interpretation report, and a plurality of tomographic images forming a three-dimensional image correspond to the medical image. In the present embodiment, it is assumed that a three-dimensional image is a CT image of a thoracoabdominal part. Specifically, the interpretation WS 3 gives an instruction to the image server 5 to request a CT image that is a target of an interpretation report to be created by the radiologist this time.

In a case where a viewing request from the interpretation WS 3 is received through the network 9, the image server 5 searches for a medical image registered in the image database 6 and transmits the searched medical image, that is, a CT image, to the interpretation WS 3 that is a request source. The interpretation WS 3 receives the CT image transmitted from the image server 5. It should be noted that the CT image received by the interpretation WS 3 is stored in the storage 13. In response to an instruction from the document creation unit 51, the analysis unit 50 acquires the medical image that is a target of the interpretation report to be created this time by searching the storage 13, and analyzes the acquired medical image.

Figure 3:
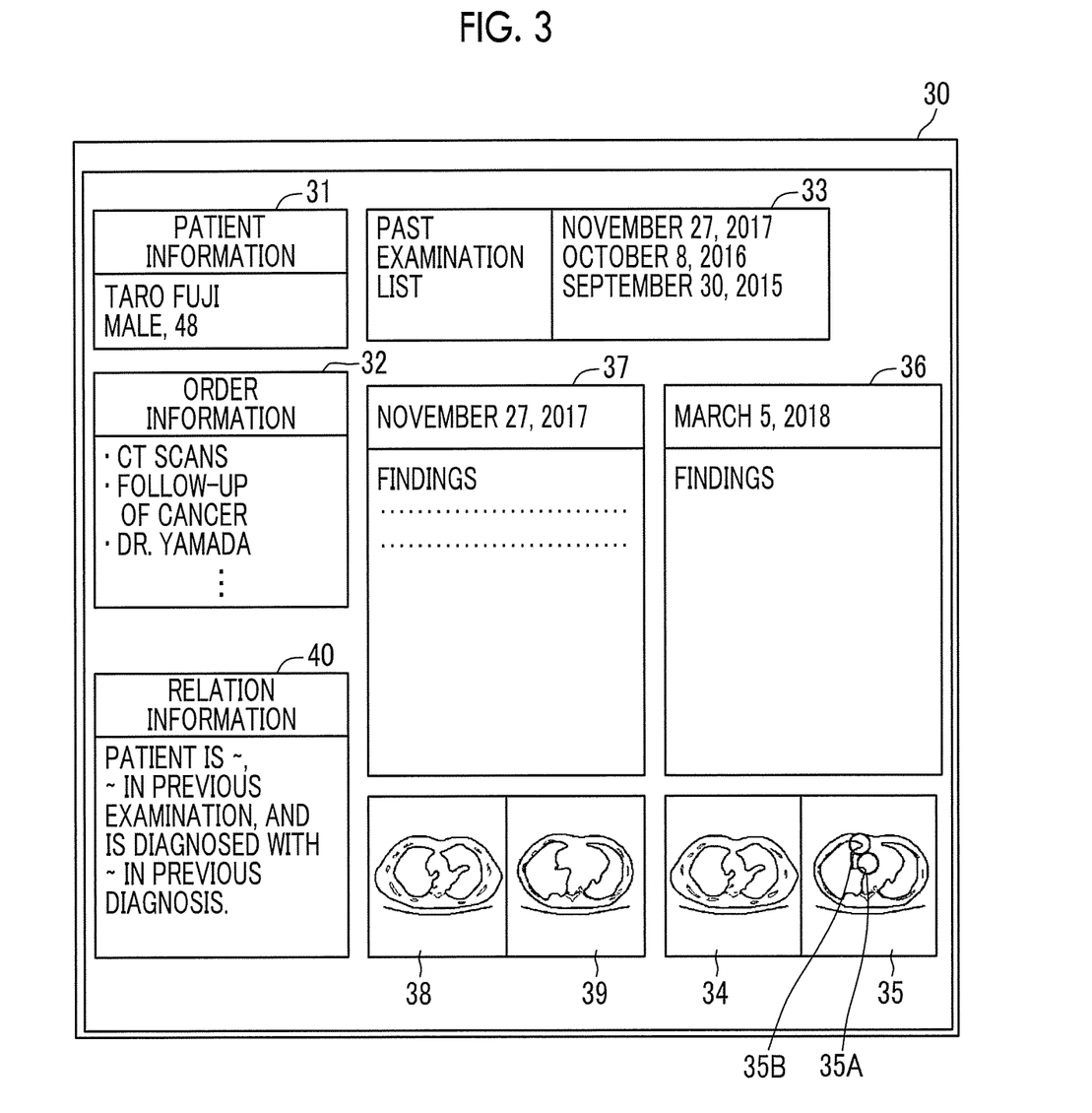
FIG. 3 is a diagram showing an interpretation report screen.

FIG. 3 is a diagram showing an interpretation report creation screen 30 displayed on a display unit 14. As shown in FIG. 3, the interpretation report creation screen 30 includes a patient information region 31 that displays patient information representing the name, gender, and the like of a patient to be imaged to acquire a CT image, an order information region 32 that displays information on an examination order for a request for an examination for acquiring the CT image, an examination list region 33 that displays a past examination list for the patient whose CT image is acquired, medical image regions 34 and 35 that display medical images to be interpreted, a creation region 36 that inputs a document for creating an interpretation report, a past interpretation report region 37 that displays a past interpretation report including character information, past image regions 38 and 39 that display a past medical image for which the interpretation report displayed in the past interpretation report region 37, and a relation information region 40 that displays relation information is created. It should be noted that the medical image displayed in the medical image region 35 on the right has superimposed marks 35A and 35B for specifying a position of the lesion specified by the analysis. The radiologist (operator) who interprets the medical image displayed in the medical image regions 34 and 35 inputs the sentence of the findings for the creation region 36 using the input unit 15. It should be noted that the relation information will be described later in detail.

The reception unit 21 receives observation information on a subject. For example, in a case where cancer is found as a result of the interpretation of the medical images displayed in the medical image regions 34 and 35 by the operator, the operator inputs the characters "the patient had cancer." from the input unit 15 as a finding to be included in the interpretation report. At this time, first, the characters "cancer" is input in hiragana, but the reception unit 21 receives the characters "cancer" consisting of six characters as the input observation information. It should be noted that in the present embodiment, the "observation information" is assumed as information representing the finding, but the present invention is not limited to thereto, and information on the subject may be used, for example, information representing a diagnosis such as "stage II lung cancer". In addition, in the present embodiment, the "observation information" is the character information of "cancer" that is, the type of lesion, but the present invention is not limited thereto, and the information may include at least one of the type of lesion such as cancer and nodule, the position of the lesion such as the lower lobe position S6b of the right lung and the lower lobe position S6 of the left lung, or the size of the lesion such as 23×19 mm and 20×10 mm.

It should be noted that in the present embodiment, the "observation information" is assumed as character information, but the present invention is not limited to character information, and includes not only character information included in a medical document but also image information representing the image information and the characters included in the medical document. In addition, the "character information" means information formed by characters included in the medical document. Further, "characters" also include a number, a symbol, and the like.

The acquisition unit 22 acquires relation information on the analysis result obtained by immediately analyzing the observation information received by the reception unit 21. Here, in the present invention, "immediately" has the same meaning as real time, and "immediately analyze" and acquisition processing by the acquisition unit 22 will be described in detail later.

The display control unit 23 causes the display unit 14 to display the interpretation report creation screen 30 including a medical image and findings. The display control unit 23 immediately displays the relation information acquired by the acquisition unit 22 in the relation information region 40 of the display unit 14. Here, in the present invention, "immediately" has the same meaning as real time, and "immediately display" and display control processing by the display control unit 23 will be described in detail later.

Figure 4:
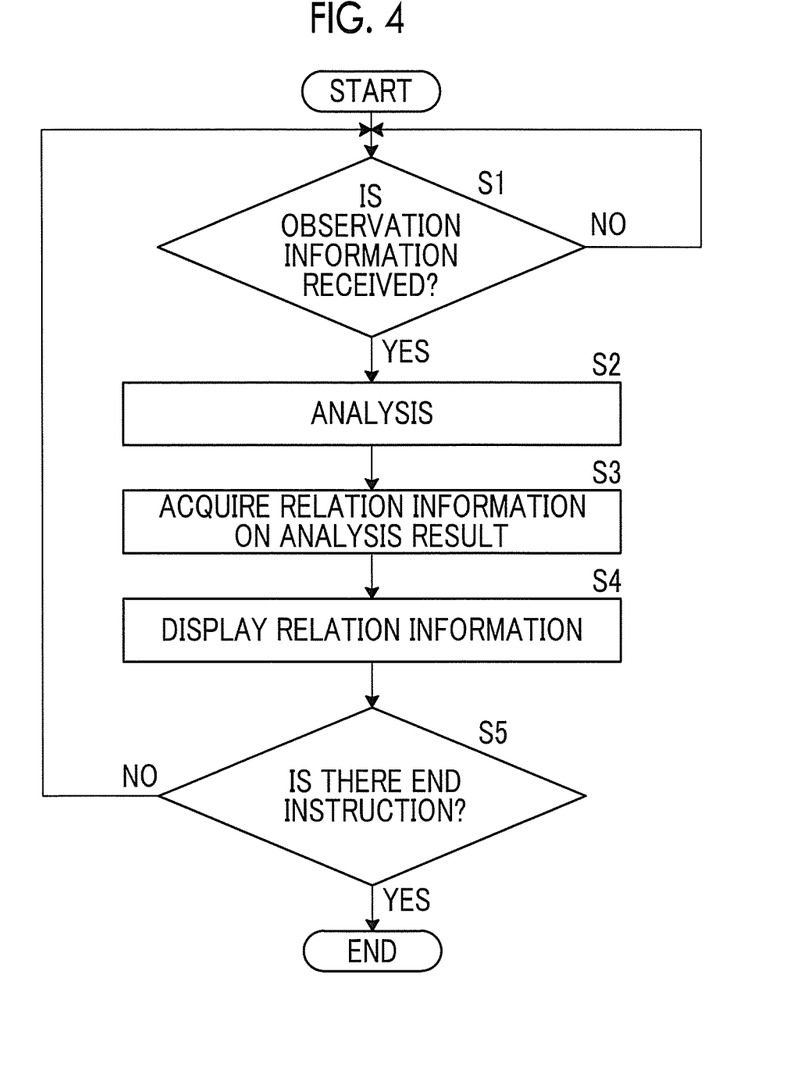
FIG. 4 is a flowchart showing medical document display control processing performed in an embodiment of the present invention.

Next, the medical document display control processing performed in the present embodiment will be described. In the present embodiment, as an example, the medical document display control processing at the time of creating an interpretation report for the medical image displayed in the medical image region 35, which is a medical image forming a CT image acquired for a subject of one examinee, will be described. It should be noted that the interpretation report created herein is assumed as a current report. FIG. 4 is a flowchart showing the medical document display control processing performed in the present embodiment.

In a case where an operator discloses a character input to the creation region 36 of the interpretation report, the document creation unit 51 starts to create the medical document. First, in step S1, the reception unit 21 discriminates whether or not the observation information is received. In a case where the observation information is not received (step S1; NO), the reception unit 21 repeats processing of step S1 until the observation information is received.

Figure 5:
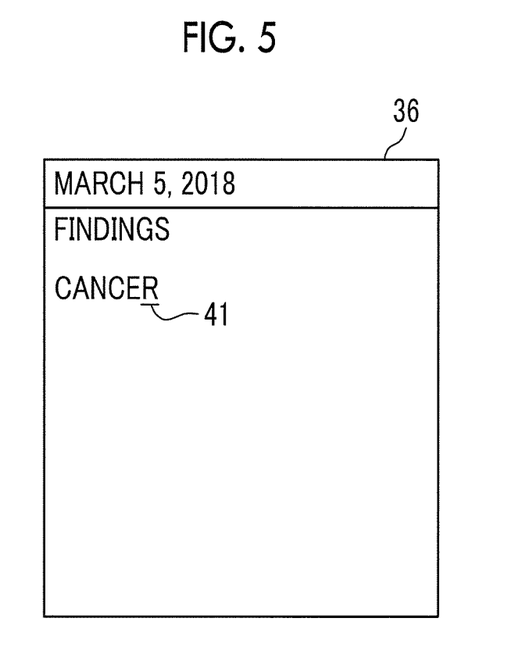
FIG. 5 is a diagram for explaining input of findings.

In a case where the observation information is received in step S1 (step S1; YES), the analysis unit 50 analyzes the observation information received by the reception unit 21 in step S2. Here, it should be noted that an analysis of the observation information by the analysis unit 50 will be described in detail later. FIG. 5 is another diagram for explaining an input of findings.

As shown in FIG. 5, the reception unit 21 receives the characters "cancer" input as described above. It should be noted that in FIG. 5, an underline existing below the final character "r" is a cursor 41. In other words, before the characters "cancer" is converted into Chinese character, and at the same time that the final character "r" is input, that is, in synchronization with the input of "r" or following the input of "r", the analysis of the characters "cancer" by the analysis unit 50 is started. In this way, the analysis unit 50 starts the analysis in synchronization with the input of the characters to the finding, so that the analysis unit 50 can perform the analysis immediately, that is, in real time, each time the finding is input.

Figure 6:
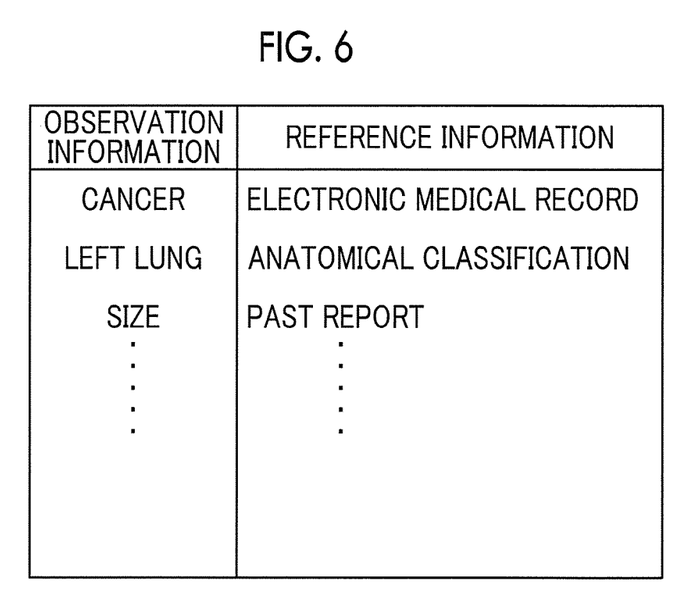
FIG. 6 is a diagram for explaining correspondence between observation information and reference information.

FIG. 6 is a diagram for explaining correspondence between observation information and reference information. As shown in FIG. 6, a correspondence table in which observation information and reference information are made to correspond to each other is stored in the storage 13 in advance. For example, in "cancer", there is a so-called familial tumor, and the "familial tumor" is a tumorous disease caused by the accumulation of tumor, that is, cancer in a family. In other words, since "cancer" has a genetic correlation, an operator such as a diagnostician or a radiologist may want to obtain information on the medical history of the subject, that is, the blood relative of the examinee. Therefore, the electronic medical record in which the information on the medical history of the blood relative is recorded is used as the reference information corresponding to "cancer".

It should be noted that in the present embodiment, the blood relative is a blood relative within the fifth degree of relation of the examinee. The time required for the analysis processing by the analysis unit 50 can be reduced by limiting the blood relative. It should be noted that regarding the blood relative, the setting can be changed by the operator, for example, a blood relative within the third degree of relation and a blood relative within the fourth degree of relation.

In addition, in a case where the observation information is the character information, for example, in a case where the observation information is a "left lung", an operator such as a diagnostician or a radiologist may want to obtain information on a region name in which the left lung is anatomically further classified as information necessary for diagnosis and interpretation. Therefore, the human body is anatomically classified, and an anatomical classification, which is information describing the names of the classified regions, is used as reference information corresponding to "left lung". It should be noted that the anatomical classification is used as reference information not only for the left lung but also for a part such as the right lung, heart, or liver that is the observation information. Here, the anatomical classification information is stored in the storage 13 in advance.

In addition, in a case where the observation information is "size", there is a case where an operator such as a diagnostician or a radiologist may want to obtain information on the past medical history including the size of the lesion, shadow, and the like in the past of the examinee as information necessary for diagnosis and interpretation, and the like. Therefore, a past report in which the information on past medical history is described, that is, an interpretation report created in the past is used as reference information of the "size".

It should be noted that in the present embodiment, the correspondence table in which the observation information and the reference information correspond to each other is used, but the present invention is not limited to thereto, and any method may be used as long as the reference information can be derived from the observation information. For example, the analysis unit 50 may have a discriminator which has been learned so as to output which reference information is the input observation information in a case where the observation information is input, and the discriminator may derive the reference information from the observation information.

The analysis unit 50 starts the analysis of the character information of "cancer" in synchronization with the reception unit 21 receiving the characters "cancer". Specifically, the analysis unit 50 uses the reference information as an electronic medical record on the basis of the correspondence table. The analysis unit 50 makes a request for an electronic medical record of a blood relative within the fifth degree of relation of the examinee (subject) to be a target of the current input finding to an electronic medical record server (not shown), and acquires data of the electronic medical record. The analysis unit 50 acquires information on the medical history of the blood relative of the examinee by analyzing the acquired electronic medical record, and acquires information on the medical history related to cancer and information on a treatment method from the information on the medical history as an analysis result.

Next, in step S3, the acquisition unit 22 acquires the relation information on the analysis result of the analysis unit 50, that is, the information on the cancer history of the blood relative of the examinee and the information on the treatment method.

Figure 7:
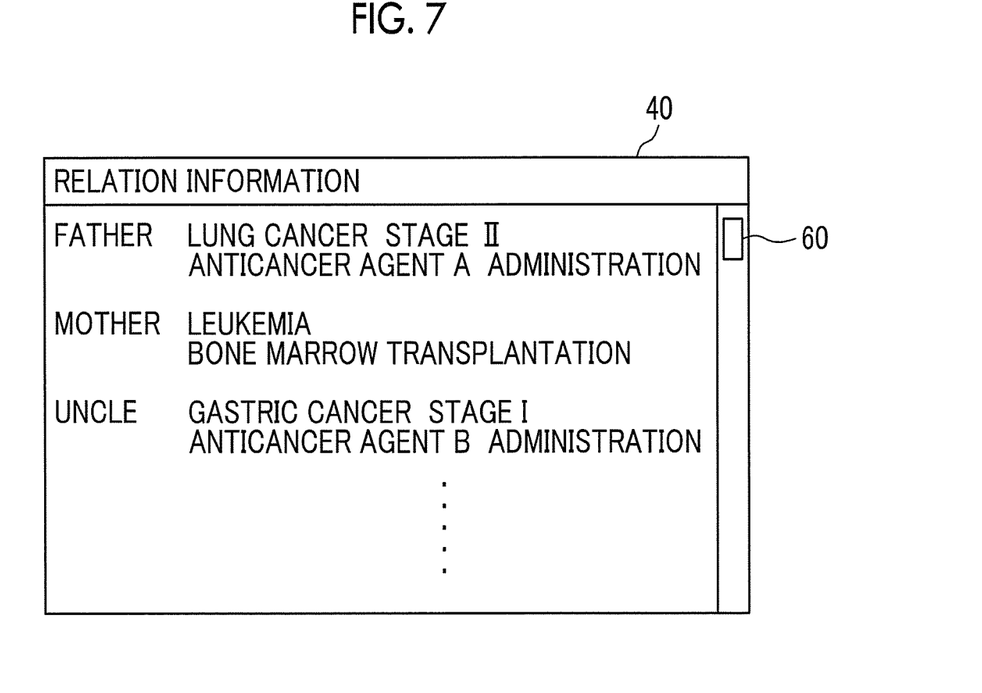
FIG. 7 is a diagram showing an example of a display of relation information.

Next, in step S4, the display control unit 23 causes the display unit 14 to immediately display the information on the cancer history of the blood relative of the examinee acquired by the acquisition unit 22 and the information on the treatment method. FIG. 7 is a diagram showing another example of a display of relation information.

The display control unit 23 causes the acquisition unit 22 to acquire the information on the cancer history of the blood relative of the examinee and the information on the treatment method, that is, in synchronization with the acquisition of the information, to display the information on the cancer history of the blood relative of the examinee and the information on the treatment method in the relation information region (refer to FIG. 3) 40 of the display unit 14, as shown in FIG. 7. Specifically, as shown in FIG. 7, the display control unit 23 causes the relation information region 40 to display that the father is in stage II of lung cancer and that an anticancer agent A has been administered. Similarly, the display control unit 23 causes the relation information region 40 to display that the mother has leukemia and has undergone bone marrow transplantation, the uncle is in stage I of gastric cancer, and an anticancer agent B has been administered.

In the present embodiment, since the acquisition unit 22 has acquired the relation information on a blood relative within the fifth degree of relation of the examinee, in a case where the relation information cannot be displayed in the relation information region 40, the display control unit 23 displays a scroll bar 60 for scrolling the displayed relation information, for example.

Figure 8:
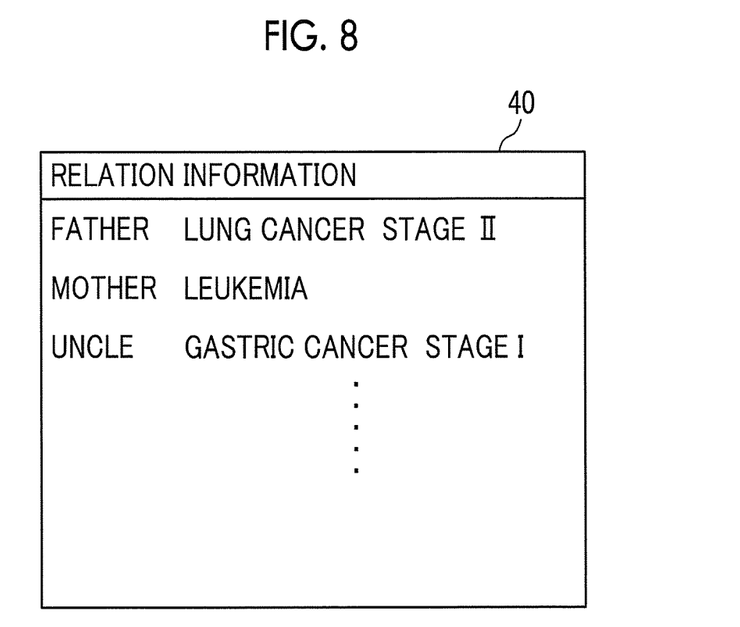
FIG. 8 is a diagram showing an example of a summary of relation information.

It should be noted that in a case where the relation information acquired by the acquisition unit 22 has an amount of information that cannot be entirely displayed in the relation information region 40, the display control unit 23 may summarize the relation information and display the summarized relation information in the relation information region 40. FIG. 8 is a diagram showing an example of a summary of the relation information.

As shown in FIG. 8, the display control unit 23 discriminates that among the relation information acquired by the acquisition unit 22, the information on the cancer history of the blood relative of the examinee is more important than the information on the treatment method, and displays the information on the cancer history of the blood relative of the examinee in the relation information region 40, and does not display the information on the treatment method. In this way, since the highly important information is displayed in the relation information region 40, the operator can easily visually recognize the highly important information.

It should be noted that in a case where the operator clicks on the type of the lesion such as "lung cancer", "leukemia", and "stomach cancer", information on each treatment method may be displayed. In addition, the display control unit 23 may summarize the relation information acquired by the acquisition unit 22 and display the summarized relation information in the relation information region 40, for example, "father, mother, uncle have the medical history".

It should be noted that with respect to the importance, information in which the importance is associated with each relation information is stored in the storage 13 in advance, and the display control unit 23 can compare the importance on the basis of the information stored in the storage 13. In addition, whether or not the information is information having high importance for the diagnosis by the diagnostician may be discriminated by using the discriminator which has been learned so as to output the probability of whether or not the information is information having high importance. Further, the relation information can be summarized by using a known automatic summarization algorithm such as Lex Rank.

In the findings, the characters "cancer" is converted into Chinese character by the operator, and in the middle of further inputting characters such as "there is", or in other words, in parallel with the operation of inputting the findings of the operator, the analysis by the analysis unit 50 in step S2, the acquisition of the relation information on the analysis result by the acquisition unit 22 in step S3, and the display of the relation information by the display control unit 23 in step S4 are performed. It should be noted that the reception unit 21 always discriminates in step S1 whether or not the observation information is received. As a result, each time an operator inputs findings, a display content of the relation information region 40 is updated immediately, that is, in real time.

For example, as shown in FIG. 8, in a case where the operator deletes the content of the finding described in the creation region 36 in a state in which the information on the cancer history of the blood relative of the examinee is displayed in the relation information region 40, the display control unit 23 deletes the display content of the relation information region 40 in synchronization with the deletion of the finding. That is, it is set as a non-display.

Figure 9:
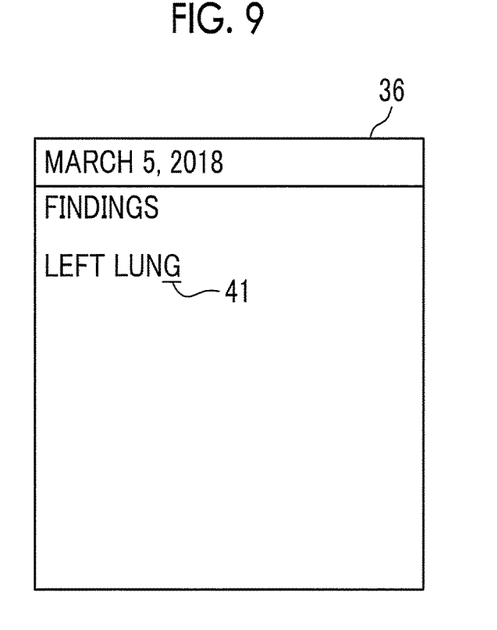
FIG. 9 is another diagram for explaining an input of findings.

In addition, as shown in FIG. 8, in a case where the content of the finding described in the creation region 36 is updated from "cancer" to another character string in a state in which the information on the cancer history of the blood relative of the examinee is displayed in the relation information region 40, the display content of the relation information region 40 is updated by the display control unit 23 in synchronization with the update. That is, the processing after step S1 in FIG. 4 is performed. FIG. 9 is another diagram for explaining an input of findings.

In step S1, the reception unit 21 newly receives the characters "left lung" as shown in FIG. 9, for example. It should be noted that in FIG. 9, an underline existing below the final character "G" is a cursor 41. In other words, before the characters "lung" is converted into Chinese character, and at the same time that the final character "g" is input, that is, in synchronization with the input of "g" or following the input of "g", the analysis of the characters "left lung" by the analysis unit 50 is started in step S2.

The analysis unit 50 uses the reference information as anatomical classification information on the basis of the above-described correspondence table. The analysis unit 50 analyzes the anatomical classification information stored in the storage 13 and acquires the name of each region anatomically classified with respect to the left lung as an analysis result. Then, in step S3, the acquisition unit 22 acquires the anatomical classification information as relation information on the analysis result of the analysis unit 50.

Figure 10:
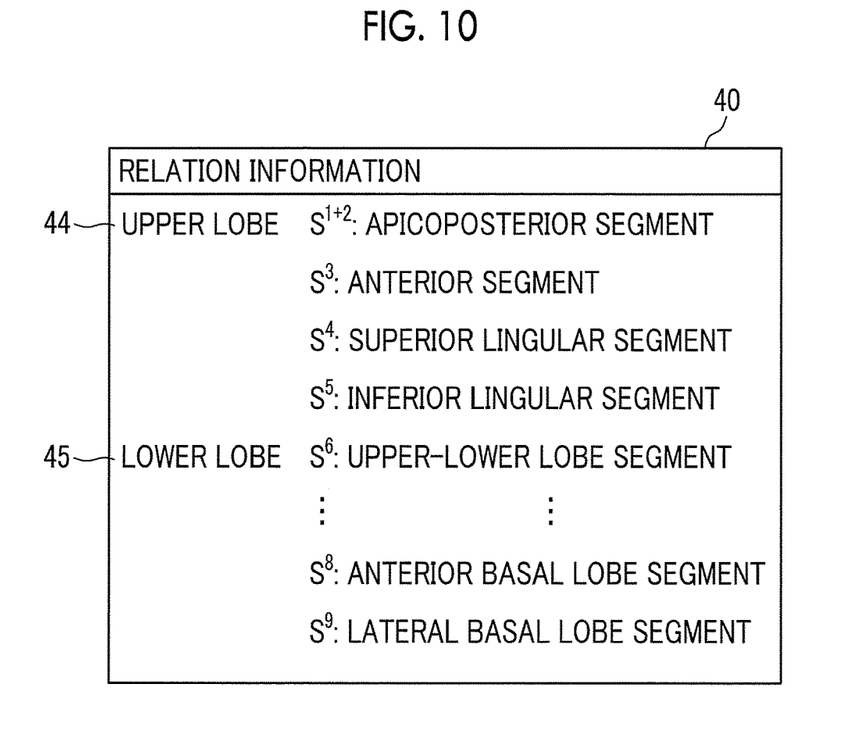
FIG. 10 is a diagram showing another example of a display of relation information.

Next, in step S4, the display control unit 23 causes the display unit 14 to immediately display the anatomical classification information acquired by the acquisition unit 22. FIG. 10 is a diagram showing another example of a display of the relation information.

At the same time that the acquisition unit 22 acquires the anatomical classification information, that is, in synchronization with the acquisition of the information, the display control unit 23 causes the relation information region 40 (refer to FIG. 3) of the display unit 14 to display the anatomical classification information as shown in FIG. 10. Here, the display control unit 23 displays each name for each anatomical classification. Specifically, as shown in FIG. 10, the display control unit 23 divides the left lung into two regions of an upper lobe 44 and a lower lobe 45, and displays the names of the regions present in each of the upper lobe 44 and the lower lobe 45. Thus, for example, in a case where the operator wants to describe in the finding that there is a nodule of 20×10 mm in the lower lobe position S6 of the left lung, the contents shown in FIG. 10 are displayed in the relation information region 40 by simply inputting the left lung, so that the operator can easily input the finding by copying the contents described in the relation information region 40 and pasting the contents into the creation region 36.

Then, in step S5, the CPU 11 determines whether or not there is an end instruction in the interpretation WS 3. In a case where there is no end instruction (step S5; NO), the CPU 11 proceeds to step S1 to continue the processing from step S1. In a case where there is the end instruction (step S5; YES), the CPU 11 ends a series of processing by the medical document display control apparatus 10.

As described above, the present embodiment includes receiving the observation information on the subject, acquiring the relation information on the analysis result obtained by immediately analyzing the received observation information, and immediately displaying the relation information on the display unit. Therefore, the relation information derived from the observation information input by the operator such as the diagnostician and the radiologist can be displayed on the display unit in real time as the information currently desired by the operator such as the diagnostician and the radiologist. Accordingly, the operator can visually recognize the desired information in real time.

It should be noted that in the present embodiment, the analysis by the analysis unit 50 is performed at the same time that the reception unit 21 receives the observation information, that is, in synchronization with the reception of the observation information by the reception unit 21, but the concept of "immediate", that is, "real time" of the present invention is not limited to thereto.

For example, the analysis unit 50 may analyze the information obtained up to the current point in time from the point in time at which the reception unit 21 starts receiving the observation information, or the analysis unit 50 may analyze the information obtained up to the current point in time from the point in time at which a certain period of time within the range of error has elapsed after the reception unit 21 starts receiving the observation information. In addition, the analysis unit 50 may analyze the information obtained from the point in time at which the reception unit 21 starts receiving the observation information to the point in time at which a certain period of time within the range of error has elapsed from the current point in time. In addition, the analysis unit 50 may analyze the information obtained from the point in time at which a certain period of time within the range of error has elapsed after the reception unit 21 starts receiving the observation information to the point in time at which a certain period of time within the range of error has elapsed from the current point in time.

Further, in the present embodiment, the display by the display control unit 23 is performed at the same time that the acquisition unit 22 acquires the relation information, that is, in synchronization with the acquisition of the relation information by the acquisition unit 22, but the concept of "immediate", that is, "real time" of the present invention is not limited thereto.

For example, the display control unit 23 may cause the display unit 14 to display at the point in time at which a certain period of time within the range of error has elapsed after the acquisition unit 22 acquires the relation information.

In addition, in the present embodiment, the medical image is assumed as a tomographic image forming a three-dimensional image that is a CT image, but the invention is not limited thereto. The three-dimensional image may be assumed as an MRI image, and the medical image may be assumed as a tomographic image forming a three-dimensional image that is an MRI image.

In addition, in the present embodiment, the present invention is applied to the case of creating an interpretation report as a medical document, but the present invention can also be applied to the case of creating medical documents other than the interpretation report such as an electronic medical record and a diagnosis report.

In addition, in the present embodiment, the analysis unit 50 that analyzes the medical image is provided in the interpretation WS 3, but the present invention is not limited to thereto. In the interpretation WS 3, analysis results analyzed by an external analysis apparatus may be acquired, and the acquired analysis results may be used to create the medical document.

In addition, in the present embodiment, the medical document is a document on the basis of the medical image obtained by imaging an examinee, but the present invention is not limited to thereto. For example, a medical document that is not created while viewing the medical image, that is, a current medical document that is not on the basis of the medical image may be used. For example, a medical certificate created by a diagnostician who examines a patient in front of the diagnostician can be used as the medical document.

In addition, in the present embodiment, the relation information is information on the subject (examinee) in the medical image, but the present invention is not limited to thereto. For example, the relation information may be information on another subject (examinee) different from the subject in the medical image. For example, the interpretation report (corresponding to the past report) about a similar case similar to the case included in the medical images displayed in the medical image regions 34 and 35 may be used as the relation information.

In this case, the interpretation WS 3 requests the past report to the interpretation report server 7. The interpretation report server 7 refers to the interpretation report database 8 and transmits the requested past report to the interpretation WS 3. In a case of extracting the past report, a method generally used in the field of artificial intelligence, that is, AI, such as machine learning, can be used.

Addition medical document display control apparatus includes a reception unit that receives observation information on a subject, an acquisition unit that acquires relation information on an analysis result obtained by the analysis started at the same time that the reception unit receives the observation information, and a display control unit that controls the display unit to display the relation information at the same time that the acquisition unit acquires the relation information.

The disclosure of JP2018-072524 filed on Apr. 4, 2018 is herein incorporated by reference in its entirety in this application.

All publications, patent applications, and technical standards described in this application are herein incorporated by reference in this application as the case in which each of publication, patent application, and the technical standard is specifically and individually described to be incorporated by reference.

What is claimed is:

1. A medical document display control apparatus comprising:
   a processor, configured to:
   receive a medical image of a subject;
   input the medical image to a machine-learning-based discriminator that discriminates whether each pixel in the medical image represents any lesion;
   obtain a discrimination result output by the machine-learning-based discriminator, wherein the discrimination result indicates the pixels in the medical image corresponding to the lesion;
   receive observation information on the subject by recognizing characters representing an interpretation of the pixels in the medical image corresponding to lesion output by the machine-learning-based discriminator;
   immediately analyze the received observation information and the discrimination result to obtain an analysis result, wherein the analysis result includes a type of the lesion, a position of the lesion in the subject, and a size of lesion which are specified through the machine-learning-based discriminator;
   determine whether the analysis result is a disease that has a genetic correlation;
   in response to the analysis result being the disease that has the genetic correlation, acquire relation information on the analysis result, wherein the acquired relation information comprises information on a medical history of a blood relative within a predetermined number of degrees of relations with respect to the subject; and
   immediately display the acquired relation information on a display.

2. The medical document display control apparatus according to claim 1,
   wherein the processor summarizes the relation information and displays the relation information on the display.

3. The medical document display control apparatus according to claim 1,
   wherein the processor displays the relation information for each item on the display.

4. The medical document display control apparatus according to claim 3,
   wherein the item is an anatomically classified region.

5. The medical document display control apparatus according to claim 3,
   wherein the item is the blood relative.

6. The medical document display control apparatus according to claim 1,
   wherein the relation information further comprises information on another subject different from the subject.

7. A medical document display control method comprising:
   receiving a medical image of a subject;
   inputting the medical image to a machine-learning-based discriminator that discriminates whether each pixel in the medical image represents any lesion;
   obtaining a discrimination result output by the machine-learning-based discriminator, wherein the discrimination result indicates the pixels in the medical image corresponding to the lesion;
   receiving observation information on the subject by recognizing characters representing an interpretation of the pixels in the medical image corresponding to lesion output by the machine-learning-based discriminator,
   immediately analyzing the received observation information to obtain an analysis result, wherein the analysis result includes a type of the lesion, a position of the lesion in the subject, and a size of lesion which are specified through the machine-learning-based discriminator;
   determine whether the analysis result is a disease that has a genetic correlation;
   in response to the analysis result being the disease that has the genetic correlation, acquiring relation information on the analysis result, wherein the acquired relation information comprises information on a medical history of a blood relative within a predetermined number of degrees of relations with respect to the subject; and
immediately displaying the acquired relation information on a display.

8. A non-transitory computer-readable storage medium storing therein a medical document display control program for causing a computer to:
receive a medical image of a subject;
input the medical image to a machine-learning-based discriminator that discriminates whether each pixel in the medical image represents any lesion;
obtain a discrimination result output by the machine-learning-based discriminator, wherein the discrimination result indicates the pixels in the medical image corresponding to the lesion;
receive observation information on the subject by recognizing characters representing an interpretation of the pixels in the medical image corresponding to lesion output by the machine-learning-based discriminator;
immediately analyze the received observation information to obtain an analysis result, wherein the analysis result includes a type of the lesion, a position of the lesion in the subject, and a size of lesion which are specified through the machine-learning-based discriminator;
determine whether the analysis result is a disease that has a genetic correlation;
in response to the analysis result being the disease that has the genetic correlation, acquire relation information on the analysis result, wherein the acquired relation information comprises information on a medical history of a blood relative within a predetermined number of degrees of relations with respect to the subject; and
immediately display the acquired relation information on a display.

* * * * *